United States Patent [19]

Kruck et al.

[11] Patent Number: 5,346,730
[45] Date of Patent: Sep. 13, 1994

[54] PROCESS FOR DEPOSITING A COPPER CONTAINING LAYER I

[75] Inventors: Thomas Kruck, Erfstadt-Bliesheim; Christian Terfloth, Cologne, both of Fed. Rep. of Germany

[73] Assignee: Kali-Chemie AG, Hanover, Fed. Rep. of Germany

[21] Appl. No.: 735,514

[22] Filed: Jul. 26, 1991

[30] Foreign Application Priority Data

Jul. 27, 1990 [DE] Fed. Rep. of Germany ....... 4023879

[51] Int. Cl.$^5$ .............................................. B05D 3/06
[52] U.S. Cl. ..................................... 427/584; 427/586; 427/109; 427/126.2; 427/126.3; 427/252; 427/253; 427/255.2; 427/255.3; 427/255.7; 427/294; 427/295; 427/322; 427/404; 427/419.2; 556/19; 556/20; 556/21; 556/26; 556/37; 556/113; 556/116
[58] Field of Search .................. 556/37, 113, 116, 117, 556/19, 20, 21, 26; 427/226, 252, 253, 53.1, 377, 255.2, 255.7, 126.3, 126.2, 108, 109, 419.2, 377, 255.3, 584, 586, 243, 294, 245, 295

[56] References Cited

U.S. PATENT DOCUMENTS

| | | | |
|---|---|---|---|
| 3,251,712 | 5/1966 | Berger | 427/229 |
| 3,256,109 | 6/1966 | Berger | 427/229 |
| 3,352,707 | 11/1967 | Pichard | 427/226 |
| 3,549,412 | 12/1970 | Frey et al. | 117/100 |
| 3,594,326 | 7/1971 | Charles et al. | 117/107.2 |
| 3,674,541 | 7/1972 | Ichiki et al. | 427/229 |
| 3,978,272 | 8/1976 | Donley | 427/226 |
| 4,666,742 | 5/1987 | Takahora et al. | 427/229 |
| 4,830,880 | 5/1989 | Okubi | 427/229 |
| 4,833,103 | 5/1989 | Agostinelli | 427/229 |
| 4,880,670 | 11/1989 | Erbil | 427/229 |

FOREIGN PATENT DOCUMENTS

| | | |
|---|---|---|
| 135179 | 3/1985 | European Pat. Off. . |
| 297348 | 1/1989 | European Pat. Off. . |
| 298345 | 1/1989 | European Pat. Off. . |

OTHER PUBLICATIONS

Schmutzler, Inorganic Chemistry, 3:415–21 (1964).
Schmutzler, Organic Syntheses, 45:99–101 (1965).
Fild et al., J. Chem. Soc.(A), 1970:2359–64 (1970).
Tsuda et al., J.A.C.S. 94:658–59 (1972).
Tsuda et al., J.A.C.S. 96:5930–31 (1974).
Tsuda et al., Inorganic Chemistry 15:2329–32 (1976).
Houle et al., Appl. Phys. Lett., 46:204–06 (1985).
Jeffries et al., Chem. Mater., 1989:8–10 (1989).
Hampden-Smith, Chem. Mater., 1990:636–39 (1990).

Primary Examiner—Janyce Bell
Attorney, Agent, or Firm—Evenson, McKeown, Edwards & Lenahan

[57] ABSTRACT

The deposition of a copper-containing layer on a substrate by decomposing, particularly by a CVD process, a compound corresponding to the formula (I)

$$RO-Cu-L \qquad (I)$$

in which
  R represents a 1-aryl lower alkyl group, a branched, optionally substituted alkyl group with 3 to 6 carbon atoms, or an aryl group, and
  L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane, is described, together with previously unknown compounds of formula (I) which may be used in the process.

29 Claims, 1 Drawing Sheet

PROCESS FOR DEPOSITING A COPPER CONTAINING LAYER I

BACKGROUND OF THE INVENTION

This invention relates to a process for depositing a copper-containing layer on a substrate and also to new copper compounds which can be used in the process of the invention.

It is known to modify substrates by surface coating so that their surface has particular functional properties. For instance, layers conducting electric current, e.g. conductive paths, can be applied to substrates.

SUMMARY OF THE INVENTION

It is an object of the present invention to provide a new process for depositing a copper-containing layer on a substrate.

A further object of the present invention is to provide new copper compounds which can be used in the process of the invention.

These and other objects of the invention are achieved by providing a process for depositing a copper-containing layer on a substrate, comprising decomposing in the presence of the substrate a compound corresponding to the formula (I)

RO—Cu—L 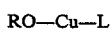 (I)

in which
R represents a 1-aryl lower alkyl group, a branched, optionally substituted alkyl group with 3 to 6 carbon atoms, or an aryl group, and
L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane, whereby a copper-containing layer is applied to the substrate.

In accordance with a further aspect of the invention, the objects are achieved by providing a compound corresponding to the formula (I)

RO—Cu—L  (I)

in which
R represents a 1-aryl lower alkyl group, a branched, optionally substituted alkyl group with 3 to 6 carbon atoms, or an aryl group, and
L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane;

with the exception of compounds in which R represents t-butyl, and L represents t-butyl isonitrile, carbon monoxide or triethylphosphane.

BRIEF DESCRIPTION OF THE DRAWINGS

The invention will be explained hereinafter in further detail with reference to the accompanying FIG. 1, which is a schematic illustration of an apparatus for carrying out the process of the invention.

DETAILED DESCRIPTION OF PREFERRED EMBODIMENTS

Figure 1:
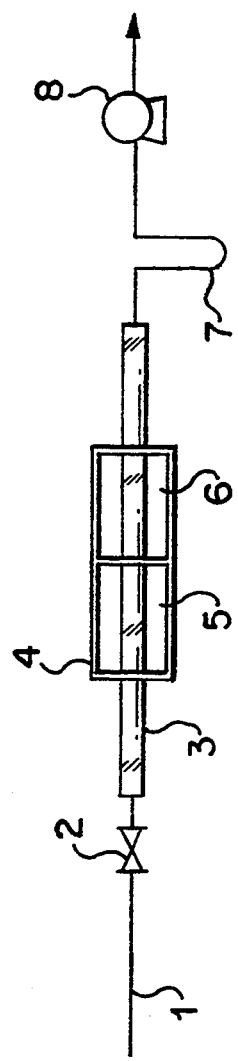

The process according to the invention for depositing a copper-containing layer on a substrate is characterized in that a copper-containing layer is applied to the substrate by decomposing a compound of the general formula RO—Cu—L (I), wherein R represents 1-aryl lower alkyl, in particular benzyl; branched, optionally substituted alkyl with 3 to 6 carbon atoms; aryl, in particular phenyl, or substituted phenyl, in particular tolyl or mesityl; and L represents (C1 to C6-alkyl)isonitrile, in particular branched alkyl isonitrile with 3 to 5 carbon atoms in the alkyl chain; aryl isonitrile, in particular phenyl isonitrile or tolyl isonitrile; carbon monoxide; dialkylaminodifluorophosphane; organyl difluorophosphane, in particular phenyl difluorophosphane or t-butyl difluorophosphane; triarylphosphane; trialkylphosphane; trifluorophosphane or trichlorophosphane.

Preferably R represents branched alkyl with 3 to 5 carbon atoms, in particular i-propyl, i-butyl, t-butyl or neopentyl, or branched alkyl with 3 to 5 carbon atoms substituted by 1 or more fluorine atoms, in particular 2-trifluoromethylpropyl or perfluoro-t-butyl.

Preferably L represents t-butyl isonitrile, carbon monoxide, triphenylphosphane or tri(lower alkyl)phosphane, in particular trimethylphosphane or triethylphosphane, or trifluorophosphane.

In order to deposit a copper-containing layer, a person skilled in the art can perform the deposition from the condensed phase or from the gas or vapor phase. It is apparent to a person skilled in the art that he can use not only a particular compound of the formula (I), but also mixtures of such compounds.

To effect deposition from the condensed phase, a person skilled in the art applies the compound of Formula (I) without solvent, or preferably dissolved in a solvent, to the substrate, and decomposes the compound. Polar or nonpolar, aprotic organic solvents, which may if desired have coordinating properties, may be used as the solvent. Suitable examples include aliphatic hydrocarbons such as pentane or petroleum spirits, aromatic hydrocarbons such as benzene or toluene, or ethers such as tetrahydrofuran.

Known methods may be used in order to apply the respective starting compound to the substrate; for instance the substrate may be dipped into the compound or a corresponding solution, the starting compound or a corresponding solution may be painted on the substrate, or preferably, the compound or a corresponding solution may be sprayed onto the substrate.

This embodiment of the process according to the invention, namely the application of the starting compound (or a corresponding mixture of starting compounds) from the condensed phase, makes it possible to coat even large surfaces very rapidly.

Subsequently, the starting compound, which has been applied to the substrate, is decomposed in order to deposit a copper-containing layer. If desired, decomposition may be effected under reduced pressure. Preferably, the decomposition is thermally induced.

This may take place by introducing the substrate coated with the starting compound into an appropriately heated chamber or by heating the substrate to the appropriate temperature range before, during and/or after the application of the starting compound.

The thermal decomposition may also be brought about by radiation-inducement, for instance by a laser which operates in the ultraviolet (UV) range, in the infrared (IR) range, or in the visible light range, and heats up the carrier.

If desired, the decomposition may also be effected by photolysis. Photolytic decomposition may be induced by a UV lamp or a laser operated at the appropriate wavelength.

The decomposition may also be plasma-induced. Various known plasma processes are suitable for this. For instance, a thermal plasma process, e.g. plasma arc or plasma jet, may be used. The pressure is then usually between 10 Torr and standard pressure.

Low-pressure plasma processes are also particularly well suited, e.g. D.C. plasma processes, glow discharge plasma processes and A.C. plasma processes, e.g. low-frequency, medium-frequency, high-frequency plasma processes and microwave plasma processes. Low-pressure processes usually operate at pressures below 10 mbar, for instance between $10^{-2}$ and 1 mbar.

The plasma-induced decomposition may be carried out in known plasma reactors. For instance, tubular, tunnel, parallel-plate and corona discharge reactors may be used. Since the decomposition in plasma may be carried out at low temperatures if desired, decomposition in plasma is well suited for coating substrates having relatively low thermal stability, for instance for coating plastics.

A person skilled in the art can influence the form in which the copper is present in the layer by adding a reactive gas. This, and the possibility of simultaneous depositing of other metals or the successive depositing of further metals, in particular of further layers having different compositions, will be explained below.

Another embodiment of the process according to the invention involves decomposition of the starting compound in the gas or vapor phase. In addition to the starting compound which is present in gaseous form, the vapor phase contains proportions of the starting compound in condensed form in a very fine distribution. Depositing from the gas or vapor phase permits the depositing of particularly well adhering, even, thin layers.

The pressure in the vapor phase or gas phase may be higher or lower. For instance, it is possible to operate at a pressure which corresponds to the vapor pressure of the starting compound used at the operating temperature. However, the total pressure may also be higher, up to standard pressure. Advantageously, the process is carried out under reduced pressure, for instance at $10^{-2}$ to 10 mbar, preferably at 0.1 to 1 mbar.

The decomposition of the starting compound in the vapor phase or gas phase is advantageously carried out in the manner of a chemical vapor deposition (CVD) process.

The principle procedures of the method of coating substrates using a CVD processes and also suitable apparatus for this purpose are known. Published European Patent Application No. EP 297,348 (which relates to coatings similar to those of the present invention) gives a person skilled in the art detailed information on how a CVD process is to be performed and which apparatus can be used.

The decomposition from the gas phase or vapor phase is advantageously performed in a pressure-tight apparatus which can be evacuated. The substrate which is to be coated is introduced into this apparatus. At reduced pressure, an atmosphere is produced which contains the copper-containing starting compound. In addition to the vaporous or gaseous starting compound, inert gas or reactive gas may be present in the gas space of the apparatus, if desired.

In one variant, the starting compound is introduced into the apparatus together with the substrate which is to be coated.

In an alternative, preferred variant, initially only the substrate is introduced into the pressure-tight apparatus and the starting compound, which already is in gaseous or vaporous form, is introduced into the apparatus continuously or discontinuously via a special line. Here too, a carrier gas may be used.

The conversion of the starting compound into the gas or vapor phase can be promoted by heating and if desired by adding a carrier gas.

The decomposition is carried out according to known methods, e.g. thermally, by the action of plasma, and/or photolytically.

The thermal decomposition from the gas or vapor phase is usually carried out by keeping the walls of the apparatus cold and heating the substrate to a temperature at which the desired copper-containing layer is deposited on the substrate. A person skilled in the art can readily determine the minimum temperature required for the compound used in each case by simple tests. Usually the temperature to which the substrate is heated will be above about 150° C.

The substrates may be heated in a conventional manner, for instance by resistance heating, inductive heating, or electric heating apparatus such as heating coils or the like. The substrates may also be heated by applying radiant energy. Laser radiation energy is particularly suitable for this. For instance, lasers may be used which operate in the visible light range, in the UV range or in the IR range. Lasers have the advantage that they can be focussed to a greater or lesser extent and can therefore specifically heat certain limited areas or points on the substrate.

Since the thermal CVD process is usually carried out at subatmospheric pressure, it is apparent to a person skilled in the art to provide pressure-tight apparatus such as are used in high-vacuum techniques. The apparatus advantageously may have gas lines which can be heated for the organometallic compound or the inert gas, openings which can be shut off for letting gas in and out, optional openings for supplying a carrier gas or reactive gas, temperature measuring means, and, if desired, an opening for supplying the organometallic compound. Means for heating the substrate must be present, as well as a pump suitable for producing the desired subatmospheric pressure, etc. If a CVD process induced by radiation energy is to be carried out, a radiation source must also be present which emits radiation in the visible light range, the infrared range or the ultraviolet range. Appropriate laser radiation energy sources are particularly suitable. The substrate can be heated by means of the radiant energy.

A very simple, advantageous apparatus for performing the process is illustrated in FIG. 1. It comprises a glass tube 3 connected to an inert gas inlet line 1 via a valve 2 which can be shut off. Tube 3 is arranged concentrically in a tubular heating furnace 4 which has two heating zones 5 and 6 ("two-zone tube furnace"). The other side of the tube is connected via a freezing trap 7 to a vacuum pump 8.

The starting compound is introduced into the first heating zone, which is located on the side of the inert gas inlet line. The substrate is introduced into the second heating zone, which is located on the side of the vacuum pump.

Plasma-induced decomposition is performed in an apparatus already described above.

Without being bound to an explanation of the formation of layers by the decomposition of the copper compounds, it is believed that gases or vapors of the copper compound reach the substrate and are decomposed thereon, forming the copper-containing layers. The thickness of the layer depends essentially on the partial pressure, on the length of the period during which deposition is carried out, and on the deposition temperature. Layers of greater or lesser thickness can be produced, for instance layers having a thickness of up to 20 micrometers, for instance between 100 Angstroms and 20 micrometers. Depending on the desired layer thickness, a person skilled in the art can determine the time and deposition temperature required to produce a copper-containing layer of a given thickness using simple tests.

As already stated, the decomposition may also be brought about photolytically, for instance by a UV lamp or a laser operating with a suitable wavelength. The use of a laser permits, for instance, the repair of conductive paths.

The gas space surrounding the substrate contains the starting compound which is present in gaseous or vaporous form. It has already been mentioned earlier that an inert gas or a reactive gas may furthermore also be contained in the gas atmosphere. Widely varying copper-containing layers are deposited, depending on the manner in which the decomposition is carried out.

If the starting compound is decomposed without the addition of an inert gas or a reactive gas, layers which contain copper essentially in metallic form are deposited upon decomposition, in particular if performed as a CVD process.

Layers which contain copper essentially in metallic form are also deposited upon thermal decomposition, in particular in a thermal CVD process, if the thermal decomposition is effected in the presence of an inert gas, for instance in the presence of noble gases such as argon.

In another embodiment, the decomposition is performed in a reactive gas atmosphere. Such a reactive gas atmosphere may of course additionally contain inert gas, for instance noble gases such as argon.

In one variant, the process is carried out in a reducing reactive gas atmosphere. The decomposition is carried out in particular in the manner of a thermal or plasma-induced CVD process. Decomposing the copper-containing starting compound in a reducing reactive gas atmosphere, particularly one which contains hydrogen, yields copper-containing layers which contain the copper essentially in metallic form.

One variant of the process according to the invention is characterized in that for depositing copper-containing layers which contain the copper substantially in the form of copper oxide, the decomposition is carried out in the presence of a reactive, hydrolysing and/or oxidizing gas atmosphere.

In order to deposit copper-containing layers which contain the copper essentially in the form of copper (I) oxide, the decomposition is performed in the presence of water vapor. In order to deposit copper-containing layers which contain the copper essentially in the form of copper (II) oxide, the decomposition is performed in the presence of an oxidizing gas atmosphere, in particular in the presence of oxygen, ozone or nitrous oxide.

In the process according to the invention, it is possible in principle to coat any substrates upon which a coating is desired. For instance, inorganic materials, such as metals or metal alloys, e.g. steel, semiconductors, silicon, insulators, ceramics, glass phases, or organic polymers, e.g. polyphenylene sulfide or polyimides, may be used as substrates.

Furthermore, it is also possible to use substrates which are also used in the production of superconductors, such as carbon, in particular carbon fibers, or for instance strontium titanate, aluminum oxide or magnesium oxide.

The deposition of layers which contain copper essentially in the form of metallic copper permits, for instance, the production of conductive paths which will conduct electric current on non-conductive substrates, for instance on ceramics or organic polymers, using known structuring processes, while masking certain areas which are not to be coated.

However, the process according to the invention offers a person skilled in the art still further possibilities. For instance, it is also suitable for depositing layers which contain one or more other metals in addition to the copper. This embodiment of the process according to the invention is characterized in that for depositing copper-containing layers which furthermore contain one or more other metals, one or more compounds of other metals, in particular compounds of aluminum, and a compound of formula (I) are decomposed simultaneously. Layers are then formed which contain copper and one or more other metals in a homogenous mixture and which are more resistant to electromigration. The simultaneous vaporization and decomposition of copper compounds of formula (I) and aluminum compounds, for instance di-i-butyl aluminum hydride, or tri-i-butyl aluminum is, for instance, suitable for producing conductive paths which are resistant to electromigration. In this embodiment it is likewise possible to operate in an inert or in a reactive gas atmosphere.

Furthermore, the person skilled in the art can also apply a plurality of different layers successively onto substrates, with at least one layer being produced according to the process of the invention.

Furthermore, it is possible, by simultaneous vaporization and decomposition of copper compounds of the general formula (I) and appropriate other vaporizable compounds in a hydrolysing and/or oxidizing atmosphere, to deposit layers which correspond in composition to known oxide ceramic high-temperature superconductors of the cuprate type. For instance, $\beta$-diketonates of yttrium, barium, strontium and other metals are used. For instance, the corresponding tetramethyl heptane dionates are suitable.

Furthermore, it is possible to deposit two or more different layers successively, with at least one of the layers having been produced according to the process of the invention.

For instance, it is possible using known methods, e.g. plasma vapor deposition (PVD) or CVD processes, to initially apply to substrates a titanium nitride layer which promotes adhesion. Then a compound of formula (I) is decomposed to form conductive paths.

This embodiment of the process according to the invention is very particularly suited for coating substrates with oxide ceramic layers which correspond in their composition to known high-temperature superconductors of the cuprate type.

Substrates which are coated with such high-temperature superconductors are known. These substrates may, for instance, take the form of fibers, strips, foils, tubes, or plates. For example, carbon fibers are used. A layer which contains copper in the form of copper oxide is applied to such a carrier by means of the process of the invention, using a compound of Formula (I), as described above.

The deposition of layers which contain the other metals contained in known oxidic superconductors, for instance yttrium and barium for producing a composition $Y_1Ba_2Cu_3O_x$, in which x has a value from 6.8 to 6.95, are produced in known manner. For instance, complex compounds of yttrium and barium with β-diketonates, in particular 2,2,6,6-tetramethyl heptane dione(3,5), may be used. For instance, yttrium-tris-2,2,6,6-tetramethyl heptane dionate(3,5) is accordingly vaporized at temperatures between room temperature and 500° C., and then this compound is decomposed at 500° C. to 700° C. A layer containing yttrium oxide is then deposited on the layer containing copper oxide which has been produced according to the process of the invention. Then, for instance, barium-bis-2,2,6,6-tetramethyl heptane dionate(3,5) is vaporized and decomposed under the same conditions. The sequence may be varied.

For conversion into a yttrium-barium-cuprate high-temperature superconductor, the coating is then tempered.

It is possible to produce modified oxide ceramic layers in a completely analogous manner by replacing part of the yttrium with strontium, lanthanum, thallium, bismuth or other metals, which advantageously are likewise used in the form of metal-β-diketonates, for instance as a metal-2,2,6,6-tetramethyl heptane dionate(3,5).

The thickness of the deposited superconductive layer is advantageously from about 5 to 20 micrometers.

A further subject of the present invention is the new compounds, which can be used in the process according to the invention, corresponding to the formula RO—Cu—L (I), in which R represents 1-aryl lower alkyl, in particular benzyl; branched, optionally substituted alkyl with 3 to 6 carbon atoms; aryl, in particular phenyl, or substituted phenyl, in particular tolyl or mesityl; and L represents (C1 to C6-alkyl)isonitrile, in particular branched alkyl isonitrile with 3 to 5 carbon atoms in its alkyl chain; aryl isonitrile, in particular phenyl isonitrile or tolyl isonitrile; carbon monoxide; dialkylaminodifluorophosphane; organyl difluorophosphane, in particular phenyl difluorophosphane or t-butyl difluorophosphane; triaryl phosphane; trialkyl phosphane; trifluorophosphane, or trichlorophosphane, with the exception of compounds in which R represents t-butyl and L t-butyl isonitrile, carbon monoxide or triethylphosphane. The three compounds t-butoxy-copper-t-butyl isonitrile, t-butoxy-copper-carbon monoxide and t-butoxy-copper-triethylphosphane are therefore excluded.

Compounds in which R represents branched alkyl with 3 to 5 carbon atoms, in particular i-propyl, i-butyl, t-butyl or neopentyl, or branched alkyl with 3 to 5 carbon atoms substituted by one or more fluorine atoms, in particular 2-trifluoromethylpropyl or perfluoro-t-butyl, are preferred.

Compounds in which L represents t-butyl isonitrile, carbon monoxide, triphenylphosphane or tri(lower alkyl)phosphane, in particular trimethylphosphane or triethylphosphane, or trifluorophosphane, are particularly preferred.

Compounds which are especially preferred include t-butoxy-copper-t-butyl difluorophosphane, t-butoxy-copper-phenyl difluorophosphane, t-butoxy-copper-diethylamino-difluorophosphane, 2-trifluoromethylpropan-2-oxy-copper-t-butyl isonitrile, 2-trifluoromethylpropan-2-oxy-copper-trimethylphosphane, perfluoro-t-butoxy-copper-t-butyl isonitrile, perfluoro-t-butoxy-copper-trimethylphosphane.

The preparation of the compounds of formula RO—Cu—L (I) will be described below.

The preparation of compounds of the formula RO—Cu—L (I), which can be used in the process according to the invention, starts with RO—Cu (II) as an intermediate product, wherein R has the meaning given above. The preparation will be described further for a preferred intermediate product, t-butoxy-copper, t—BuO—Cu (III). T. Tsuda, T. Hashimoto and T. Saegusa in J. A. C. S. 94 (1972), pages 658 and 659, describe the preparation of this intermediate product from anhydrous copper (I) chloride and t-BuO-Li in tetrahydrofuran at room temperature under inert gas. Perfluoro-t-butoxy-copper (IV) and 2-trifluoromethyl-propan-2-oxy-copper (V) are prepared in an analogous manner. Intermediate compounds having different radicals R can also be prepared analogously.

The intermediate products of formulae (II), (III), (IV) or (V) obtained in this manner are then dissolved in an aprotic, non-polar organic solvent, such as benzene or cyclohexane, and a preferably equimolar quantity of the ligand L is added thereto, whereupon a compound of the formula RO—Cu—L (I) is formed.

The ligands L and their preparation are known. Some of these ligands L are commercially available products, for instance t-butyl isonitrile, trimethylphosphane, triethylphosphane, triphenylphosphane, trifluorophosphane or trichlorophosphane, or carbon monoxide.

Other ligands L may be prepared in known manner. Phenyl difluorophosphane and the preparation thereof are described, for instance, by R. Schmutzler, in Chem. Bet. 98 (1965), pages 552 to 556. The synthesis starts with phenyl dichlorophosphane, which itself is a commercially available product, or which can be obtained by adding phosphorus pentachloride and styrene and reducing with sulfur dioxide, see R. Schmutzler in Org. Syn. 45 (1965), pages 99 to 101. Phenyl dichlorophosphane is reacted with sodium fluoride in tetramethylene sulfone, and the mixture is heated to 140° to 180° C. The desired phenyl difluorophosphane is then isolated from the mixture by distillation at reduced pressure.

The preparation of t-butyl difluorophosphane is described by M. Fild and R. Schmutzler in J. Chem. Soc. (A) 1970, pages 2359 to 2364. The synthesis starts with t-butyl dichlorophosphane, which is obtained by reacting phosphorus trichloride with t-butyl magnesium chloride. The intermediate product is converted to the desired t-butyl difluorophosphane with antimony trifluoride or sodium fluoride in sulfolane and is then isolated by distillation.

Other organyl difluorophosphanes are likewise advantageously prepared from the corresponding organyl dichlorophosphanes. The preparation of such organyl dichlorophosphanes, in which "organyl" represents an alkyl group with 1 to 4 carbon atoms which is unsubstituted or substituted by halogen, or in which "organyl" represents optionally substituted phenyl, is described, for instance, in Houben-Weyl, Methoden der organischen Chemie, Vol. XII/1, organische Phosphorverbindungen, Part 1, pages 302 to 318. In particular, these compounds are prepared by reacting phosphorus trichloride with organometallic compounds, for instance alkyl mercury, alkyl cadmium, alkyl lead or alkyl aluminum compounds or corresponding aryl compounds. The resulting organyl dichlorophosphane is then fluorinated with sodium fluoride or antimony trifluoride as described above.

Dialkylaminodifluorophosphane compounds and their preparation are likewise known. In this context, "alkyl" refers to lower alkyl with 1 to 3 carbon atoms, in particular methyl or ethyl. The term dialkylamine also comprises the compound piperidine. Such compounds can be prepared, for instance, by fluorinating the corresponding dialkylaminodichlorophosphanes with antimony trifluoride or sodium fluoride in sulfolane, as described by R. Schmutzler in Inorg. Chem. 3 (1964), pages 415 to 421. The dialkylaminodichlorophosphane compounds may be prepared from phosphorus trichloride and the corresponding dialkylamine.

The present invention also relates to the compounds 2-trifluoromethylpropan-2-oxy-copper and perfluoro-t-butoxy-copper, which are valuable intermediate products for the preparation of corresponding compounds according to the invention of the formula RO—Cu—L (I), wherein R represents 2-trifluoromethylpropyl or perfluoro-t-butyl.

These intermediate products are prepared as described above by converting 2-trifluoromethylpropan-2-ol or perfluoro-t-butanol with n-butyl lithium into 2-trifluoromethylpropan-2-oxy lithium or perfluoro-t-butoxy lithium, respectively, and then reacting with Cu(I)Cl to form the desired intermediate product.

The compounds used in the process of the invention have substantial advantages compared with prior art compounds, e.g. they can be handled better at room temperature, they are more readily accessible, and they have a lower decomposition temperature. Thus gentler deposition of copper-containing layers on temperature-sensitive substrates is facilitated. Isonitrile compounds are particularly advantageous due to their ability to readily decompose photolytically.

The following examples are intended to illustrate the invention in further detail without restricting its scope.

EXAMPLE 1

Preparation of t-BuO-Cu

The preparation took place as described by T. Tsuda et al in Inorg. Chem. 15 (1976), pages 2331 to 2332.

The preparation was carried out directly in a subliming apparatus. 5.0 g anhydrous Cu(I)Cl and 3.7 g lithium-t-butoxide were dissolved in 50 ml dried, oxygen-free tetrahydrofuran and stirred overnight at ambient temperature under a nitrogen atmosphere. The solvent was evaporated at reduced pressure, and the remaining solid was sublimed at 170° C. and 0.8 mm. The yield was approximately 5 g yellow crystals of t-butoxy-copper.

The experiment was repeated several times in order to obtain larger quantities of this compound.

EXAMPLE 2

Preparation of 2-trifluoromethylpropan-2-oxy-copper 5 g 2-trifluoromethylpropan-2-ol were lithiated with an equimolar quantity of lithium-t-butoxide, and the reaction product was dissolved in 50 ml anhydrous, oxygen-free tetrahydrofuran. An equimolar quantity of Cu(I)Cl was added to the solution, and the mixture was stirred overnight at ambient temperature under a nitrogen atmosphere. The lithium chloride which was precipitated was filtered out, and volatile constituents were evaporated. The yield of 2-trifluoromethylpropan-2-oxy-copper was quantitative.

$^1$H-NMR-spectrum: 1.29 ppm (Singlet)
$^{19}$F-NMR-spectrum: −84.79 ppm
IR spectrum (Nujol):
  1134 cm$^{-1}$
  1047 cm$^{-1}$
  1007 cm$^{-1}$
  611 cm$^{-1}$
  509 cm$^{-1}$

EXAMPLE 3

Preparation of perfluoro-t-butoxy-copper

This compound was prepared analogously to the preparation of the trifluoromethylpropoxy compound described in Example 2.

EXAMPLE 4

Preparation of t-BuO-Cu-CO

The preparation took place as described by T. Tsuda et al in J. Am. Chem. Soc. 96 (1974), pages 5930 and 5931.

4.5 g of the t-BuO-Cu prepared according to Example 1 were suspended in benzene, and carbon monoxide was passed through the suspension at room temperature. Once the solid had dissolved completely, the solution was filtered, the benzene was evaporated, and the remaining solid was sublimed at 60° C. (1 mm). The yield of t-BuO-Cu-CO was approximately 75% of the theoretical yield.

EXAMPLE 5

Preparation of t-BuO-Cu-t-BuNC

The preparation took place as described by T. Tsuda et al. in J. Am. Chem. Soc. 96 (1974), pages 5930 and 5931.

4.5 g of the t-BuO-Cu prepared according to Example 1 were suspended in benzene, and an equimolar quantity of t-BuNC was added. The solvent was evaporated, and the solid residue was sublimed at 90° C. (1 mm). The yield of t-BuO-Cu-t-BuNC was approximately 75% of the theoretical yield.

EXAMPLE 6

Preparation of t-BuO-Cu-PEt$_3$

The preparation took place as described by T. Tsuda et al. in J. Am. Chem. Soc. 94 (1972), pages 658 and 659.

4.3 g of the t-BuO-Cu prepared according to Example 1 were suspended in benzene, and an equimolar quantity of triethylphosphane was added. The solvent was evaporated, and the remaining solid was sublimed at 100° C. (1 mm). The yield was approximately 80% of the theoretical yield.

EXAMPLE 7

Preparation of 2-trifluoromethylpropan-2-oxy-copper-t-butyl isonitrile

An equimolar quantity of t-butyl isonitrile was added to 3.5 g of 2-trifluoromethylpropan-2-oxy-copper prepared according to Example 2 in benzene. The mixture was stirred further until the suspended solid had completely dissolved. Then readily volatile constituents were evaporated. The yield of 2-trifluoromethylpropan-2-oxy-copper-t-butyl isonitrile was approximately quantitative.

$^1$H-NMR-spectrum:
  1.29 ppm O—C(CH$_3$)$_2$(CF$_3$)
  1.45 ppm C(CH$_3$)
$^{19}$F-NMR-spectrum: —84.67 ppm (CF$_3$)
IR spectrum (Nujol):
  2176 cm$^{-1}$
  1369 cm$^{-1}$
  1240 cm$^{-1}$
  1192 cm$^{-1}$ The product may be further purified by sublimation. The yield after sublimation was approximately 80% of the theoretical yield.

EXAMPLE 8

Preparation of 2-trifluoromethylpropan-2oxy-copper-trimethylphosphane 4.8 g of the 2-trifluoromethylpropan-2-oxy-copper prepared according to Example 2 was suspended in benzene, and an equimolar quantity of trimethylphosphane was added thereto. Once the solid had dissolved, the solvent was evaporated. The compound 2-trifluoromethylpropan-2-oxy-copper-trimethylphosphane, a solid, was isolated in an approximately quantitative yield.

$^1$H-NMR-spectrum:
  1.29 ppm —O—C(CH$_3$)$_2$(CF$_3$)
  1.21–1.23 ppm —C(CH$_3$)$_3$
$^{19}$F-NMR-spectrum: —84.69 ppm (CF$_3$)
$^{31}$P-NMR-spectrum: —45.89 ppm
IR spectrum (KBr pressed body):
  2963 cm$^{-1}$
  2901 cm$^{-1}$
  1425 cm$^{-1}$
  951 cm$^{-1}$
  727 cm$^{-1}$ If desired, the compound may be purified further by sublimation. The yield after sublimation was approximately 70% of the theoretical yield.

EXAMPLE 9

Use of compounds of Formula (I) for depositing copper-containing layers

An apparatus constructed corresponding to FIG. 1 was used. A quartz glass tube was introduced concentrically into a two-zone tube furnace. One side of the quartz tube was closably connected to an inert gas line, the other side to a vacuum pump. Between the quartz tube and the vacuum pump there was a trap which could be chilled in order to separate volatile constituents from the gas stream pumped out of the tube.

The organometallic compound to be vaporized was positioned in a porcelain boat in the glass tube in the first heating zone of the two-zone tube furnace. The substrate was introduced into the second heating zone. In one example of application, the glass tube wall in the second heating zone also served simultaneously as the substrate.

9.2 Performance of the test
9.2.1 Use of glass as substrate

The quartz glass tube wall acted as the substrate. The t-BuO-Cu-t-BuNC prepared according to Example 5 was used as the starting compound.

The heating zone 2 was heated to approximately 400° C. The pressure was approximately 1 mbar. The starting compound introduced into the quartz tube was heated to 110° C. The starting compound crossed into the gas atmosphere and was passed through the quartz tube while introducing a stream of nitrogen (approximately 25 ml/min) into the quartz tube.

After approximately 30 minutes, the deposition was complete, and the glass tube was brought to standard pressure with purified nitrogen introduced via the inert gas line. A layer of copper had been deposited on the glass tube in heating zone 2.

9.2.2 Use of polyimide as substrate

The t-BuO-Cu-CO prepared according to Example 4 was used as the starting compound. The test was performed as described in Example 9.2.1. The substrate was introduced into heating zone 2. The temperature in heating zone 1 was set at 60° C. and that in heating zone 2 at 400° C. After the sample had been removed from the quartz tube, it was found that an adherent copper layer had again been formed on the polyimide.

9.2.3. Use of polyimide as substrate

The t-BuO-Cu-PEt$_3$ prepared according to Example 6 served as the starting compound. The test was performed as described in Example 9.2.2. The temperature in heating zone 1 was set at 120° C., and that in heating zone 2 at 400° C. After the sample had been removed from the quartz tube, it was found that a well adhering copper layer had again been formed on the polyimide.

9.2.4. Use of silicon discs as substrate

The starting compound was the 2-trifluoromethylpropan-2-oxy-copper-t-butyl isonitrile prepared according to Example 7. The test was performed as described in Example 9.2.2. The temperature in heating zone 1 was set at 115° C., and at 400° C. in heating zone 2. After the sample had been removed from the quartz tube, it was found that a copper layer which adhered very well had been formed on the silicon discs.

9.2.5. Use of polyimide as substrate

The starting compound was the 2-trifluoromethylpropan-2-oxy-copper-trimethylphosphane prepared according to Example 8. The test was performed as described in Example 9.2.2. The temperature in heating zone 1 was set at 125° C., and at 400° C. in heating zone 2. After the sample had been removed from the quartz tube, it was found that a copper layer which adhered very well had again been formed on the polyimide.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A process for depositing a copper-containing layer on a substrate, said process comprising decomposing in the gas or vapor phase and in the presence of said substrate a compound corresponding to the formula (I)

$$RO—Cu—L \qquad (I)$$

wherein
  R represents a 1-aryl lower alkyl group, a branched, optionally substituted alkyl group with 3 to 6 carbon atoms, or an aryl group, and
  L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane, whereby a copper-containing layer is applied to said substrate.

2. A process according to claim 1, wherein R represents a branched alkyl group with 3 to 5 carbon atoms or a branched alkyl group with 3 to 5 carbon atoms substituted by at least one fluorine atom.

3. A process according to claim 2, wherein R represents an i-propyl, i-butyl, t-butyl, neopentyl, 2-trifluoromethylpropyl, or perfluoro-t-butyl group.

4. A process according to claim 1, wherein R represents a benzyl, phenyl, tolyl, or mesityl group.

5. A process according to claim 1, wherein L represents t-butyl isonitrile, carbon monoxide, triphenylphosphane, tri(lower alkyl)phosphane, or trifluorophosphane.

6. A process according to claim 5, wherein L represents trimethylphosphane or triethylphosphane.

7. A process according to claim 1, wherein L represents a branched alkyl isonitrile with 3 to 5 carbon atoms in its alkyl chain, phenyl isonitrile, tolyl isonitrile, phenyl difluorophosphane, or t-butyl difluorophosphane.

8. A process according to claim 1, wherein said decomposing step is effected thermally or by applying radiant energy to said compound of formula (I).

9. A process according to claim 8, wherein said decomposing step is effected by applying laser radiation to said compound of formula (I).

10. A process according to claim 8, wherein said decomposing step is effected thermally by heating said substrate to a temperature above about 150° C.

11. A process according to claim 1, wherein said compound of formula (I) is converted into the vapor phase and decomposed under reduced pressure.

12. A process according to claim 11, wherein said compound of formula (I) is converted to the vapor phase while entrained in a carrier gas.

13. A process according to claim 1, wherein said substrate is composed of an inorganic material selected from the group consisting of metals, semiconductors, ceramics, and glass phases.

14. A process according to claim 1, wherein said substrate is composed of an organic material selected from the group consisting of polyphenylene sulfide polymers, polyimide polymers, and carbon fibers.

15. A process for depositing a copper-containing layer on a substrate, said process comprising decomposing in the presence of said substrate a compound corresponding to the formula (I)

RO—Cu—L  (I)

wherein
R represents a 1-aryl lower alkyl group a branched, optionally substituted alkyl group with 3 to 6 carbon atoms, or an aryl group, and
L represents (C1 to C6-alkyl)isonitrile aryl isonitrile, carbon monoxide, dialkylaminodifluorophosphane, organyl difluorophosphane, triaryl phosphane, trialkyl phosphane, trifluorophosphane, or trichlorophosphane, wherein said decomposing step is effected under an inert gas atmosphere or a reducing gas atmosphere, whereby a copper-containing layer containing copper essentially in the form of metallic copper is deposited on said substrate.

16. A process for depositing a copper-containing layer on a substrate, said process comprising decomposing in the presence of said substrate a compound corresponding to the formula (I)

RO—Cu—L  (I)

wherein
R represents a 1-aryl lower alkyl group, a branched, optionally substituted alkyl group with 3 to 6 carbon atoms, or an aryl group and
L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane, wherein said decomposing step is effected in the presence of a reactive oxidizing or hydrolyzing gas atmosphere, whereby a copper-containing layer containing copper essentially in the form of copper oxide is deposited on said substrate.

17. A process for depositing a copper-containing layer on a substrate, said process comprising decomposing in the presence of said substrate a compound corresponding to the formula (I)

RO—Cu—L  (I)

wherein
R represents a 1-aryl lower alkyl group, a branched, optionally substituted alkyl group with 3 to 6 carbon atoms, or an aryl group, and
L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane, wherein said compound of formula (I) and at least one compound of at least one metal other than copper are decomposed, thereby to deposit layers containing copper and at least one other metal on said substrate.

18. A process according to claim 17, wherein said compound of a metal other than copper is an aluminum compound.

19. A process according to claim 17, wherein a plurality of different layers are deposited successively.

20. A process according to claim 17, wherein said compound of formula I and said at least one compound of at least one metal other than copper are decomposed simultaneously to form a layer containing copper and at least one other metal.

21. A compound corresponding to the formula (I)

RO—Cu—L  (I)

wherein
R represents a 1-aryl lower alkyl group, a branched, optionally substituted alkyl group with 3 to 6 carbon atoms, or an aryl group, and
L represents (C1 to C6-alkyl)isonitrile, aryl isonitrile, carbon monoxide, dialkylaminodifluorophosphane, organyl difluorophosphane, triaryl phosphane, trialkyl phosphane, trifluorophosphane, or trichlorophosphane; with the exception of compounds in which R represents t-butyl, and L represents t-butyl isonitrile, carbon monoxide or triethylphosphane.

22. A compound according to claim 21, wherein R represents a branched alkyl group with 3 to 5 carbon atoms or a branched alkyl group with 3 to 5 carbon atoms substituted by at least one fluorine atom.

23. A compound according to claim 22, wherein R represents an i-propyl, i-butyl, t-butyl, neopentyl, 2-trifluoromethylpropyl, or perfluoro-t-butyl group.

24. A compound according to claim 21, wherein R represents a benzyl, phenyl, tolyl, or mesityl group.

25. A compound according to claim 21, wherein L represents t-butyl isonitrile, carbon monoxide, triphenylphosphane, tri(lower alkyl)phosphane, or trifluorophosphane.

26. A compound according to claim 25, wherein L represents trimethylphosphane or triethylphosphane.

27. A compound according to claim 21, wherein L represents a branched alkyl isonitrile with 3 to 5 carbon atoms in its alkyl chain, phenyl isonitrile, tolyl isonitrile, phenyl difluorophosphane, or t-butyl difluorophosphane.

28. A compound according to claim 21, selected from the group consisting of:
   t-butoxy-copper-t-butyl difluorophosphane,
   t-butoxy-copper-phenyl difluorophosphane,
   t-butoxy-copper-diethylaminodifluorophosphane,
   2-trifluoromethylpropan-2-oxy-copper-t-butyl isonitrile,
   2-trifluoromethylpropan-2-oxy-copper-trimethylphosphane,
   perfluoro-t-butoxy-copper-t-butyl isonitrile, and
   perfluoro-t-butoxy-copper-trimethylphosphane.

29. 2-trifluoromethylpropan-2-oxy-copper or perfluoro-t-butoxy-copper.

* * * * *